United States Patent [19]

Van Den Bosch

[11] Patent Number: 5,208,024
[45] Date of Patent: May 4, 1993

[54] **VACCINE AGAINST *E. COLI* SEPTICAEMIA IN POULTRY**

[75] Inventor: Johannes F. Van Den Bosch, Boxmeer, Netherlands

[73] Assignee: Akzo NV, Arnhem, Netherlands

[21] Appl. No.: 764,991

[22] Filed: Sep. 23, 1991

Related U.S. Application Data

[63] Continuation of Ser. No. 255,806, Oct. 11, 1988.

[30] Foreign Application Priority Data

Oct. 26, 1987 [NL] Netherlands ............. 87.02536

[51] Int. Cl.$^5$ .................... A61K 39/00; A61K 39/02
[52] U.S. Cl. ............................ 424/92; 424/88
[58] Field of Search ......................... 424/92, 88

[56] References Cited

U.S. PATENT DOCUMENTS

| | | | |
|---|---|---|---|
| 4,725,435 | 2/1988 | Brinton, Jr. et al. | 424/92 |
| 4,736,017 | 4/1988 | O'Hanley et al. | 424/92 |
| 4,740,585 | 4/1988 | Schmidt et al. | 530/806 |

FOREIGN PATENT DOCUMENTS

| | | |
|---|---|---|
| 0060129 | 9/1982 | European Pat. Off. |
| 0087735 | 7/1983 | European Pat. Off. |
| 8603410 | 6/1986 | European Pat. Off. |
| 8604604 | 8/1986 | European Pat. Off. |

OTHER PUBLICATIONS

Roberts J. of Urology 131:602–607, Prevention of Pyelonephritis by Immunization with P-Fimbriae 1954.
de Ree Feus Micro., 29:91–97 1985.
de Ree J. of Chemical Micro 24:121–125 1986.
Arp et al. Avian Disease 24:153–161 Piliation Hemagglutination, Motilit, & Generation Time of *E. coli* 1979.
Silverblatt The J of Clinc. Inv. 64:333–336 1979 Antipili Antibody Affords Protection Against Experimental Ascending Pyelonephritis.
de Ree et al. I & I 50:900–904 1985 (1).
de Ree et al., *FEMS Microbiology Letters*, vol. 29, pp. 91–97, 1985.
de Ree et al., *J. Clin. Microbiol.*, vol. 24, pp. 121–125, Jul. 1986.
van Die et al., Academic Press Inc. (London) Ltd., pp. 39–46, 1986.
Hopp et al., *Proc. Natl. Acad. Sci. U.S.A.*, vol. 78, No. 6 pp. 3824–3828, Jun., 1981.
Van Die et al., *Microbiol Pathogenesis*, vol. 3, pp. 149–154, 1987.
de Ree et al., FEMS Microbiol. Letter, vol. 26, No. 2, pp. 163–169, 1985.
de Ree et al., *Infect. Immun.*, vol. 50, No. 3, pp. 900–904, Dec. 1985.
Van Der Bosch et al., *J. Med. Microbiol.*, vol. 14, No. 3, pp. 321–331, 1981.
Waalwijk et al., *FEMS Microbiology Letters*, vol. 19, No. 3, pp. 171–175, 1982.
Chem Abstracts, vol. 104, No. 25, Jun. 23, 1986 (Columbus, Ohio, U.S.) R. E. Isaacson: "Development of Vaccines for Bacterial Diseases Using Recombinant DNA Technology".
Chem Abstracts, vol. 104, No. 15, Apr. 14, 1986 (Columbus, Ohio, U.S.) J. K. Pedersen et al.: "987P Fimbriae from Porcine Enterotoxigenic Escherichia coli, etc.".

*Primary Examiner*—Christine M. Nucker
*Assistant Examiner*—H. Sidberry
*Attorney, Agent, or Firm*—William M. Blackstone

[57] ABSTRACT

The present invention is concerned with vaccines effective in protecting poultry against *E. coli* septicaemia, which contain or can cause the production of fimbriae of the F11 type or an immunogenic section thereof, or antibodies against these.

1 Claim, 2 Drawing Sheets

Figure 1
Amino acid sequence of F11 subunit

1

<u>Ala Pro Thr Ile Pro Gln Gly Gln Gly Lys Val Thr Phe Asn Gly</u>

16

<u>Thr Val</u> Val Asp Ala Pro Cys Ser Ile Ser Gln Lys Ser Ala Asp

31

Gln Ser Ile Asp Phe Gly Gln Leu Ser Lys Ser Phe Leu Glu Ala

46

Gly Gly Thr Ser Lys Pro Met Asp Leu Asp Ile Glu Leu Val Asn

61

Cys Asp Ile Thr Ala Phe Lys Gln Gly Gln Ala Ala Lys Asn Gly

76

Lys Val Gln Leu Ser Phe Thr Gly Pro Glu Val Thr Gly Gln Ala

91

Glu Glu Leu Ala Thr Asn Gly Gly Thr Gly Thr Ala Ile Val Val

106

Gln Ala Ala Gly Lys Asn Val Ser Phe Asp Gly Thr Ala Gly Asp

121

Ala Tyr Pro Leu Lys Asp Gly Asp Asn Val Leu His Tyr Thr Ala

136

Leu Val Lys Lys Ala Asn Gly Gly Thr Val Ser Glu Gly Ala Phe 151                                                      161

Ser Ala Val Ala Thr Phe Asn Leu Ser Tyr Gln

VACCINE AGAINST E. COLI SEPTICAEMIA IN POULTRY

This is a continuation of application Ser. No. 07/255,806 filed Oct. 11, 1988.

The invention relates to a vaccine for protecting poultry against *Escherichia coli* (*E. coli*) septicaemia and also to a method for combating *E. coli* septicaemia in poultry by administering such a vaccine.

BACKGROUND OF THE INVENTION

*E. coli* septicaemia or colibacillosis is a disease which generally occurs in poultry (such as chickens and turkeys) and which is responsible for considerable losses. Characteristic symptoms in birds having this disease are air sac inflammation, pericarditis and perihepatitis. Most of the investigations in this field reveal that more than half of the *E. coli* strains which are encountered in said sick birds belong to one of three serotypes 01:K1, 02:K1 or 078:K80. In the United States, the serotype 035 is also frequently encountered. It is generally assumed that *E. coli* septicaemia is a secondary infection which enters the body via the respiratory tract after it has been damaged, for example, by viruses which cause respiratory diseases or by mycoplasmas.

Little is known of the virulence factors which play a role in the pathogenesis of colibacillosis in poultry. The virulence factors of *E. coli* strains which play a role in infections in mammals include, for example, attachment fimbriae, toxins and iron-sequestrating mechanisms.

Many different attachment fimbriae, which are generally highly host-specific, have been described. Thus, the CFA fimbriae have been encountered in humans with diarrhoea, K88 fimbriae in piglets with diarrhoea, K99 in sheep, calves and piglets with diarrhoea, and P fimbriae (including those of the F11 type) in humans with urinary tract infections. It has been found, in addition, that administration of said types of attachment fimbriae in purified form as a vaccine resulted in a protective immune response in the respective type of animal. However, a similar virulence factor has not been identified for colibacillosis in poultry.

SUMMARY OF THE INVENTION

A vaccine has now been found for protecting poultry against *E. coli* septicaemia which is characterized in that it contains fimbriae of the F11 type or an immunogenic section thereof, or organisms in which there is genetic material which codes for the production and, optionally, excretion of said fimbriae or an immunogenic section thereof.

BRIEF DESCRIPTION OF THE DRAWINGS

FIG. 1 illustrates the amino acid sequence of a F11 subunit.

DESCRIPTION OF THE PREFERRED EMBODIMENTS

Figure 2:
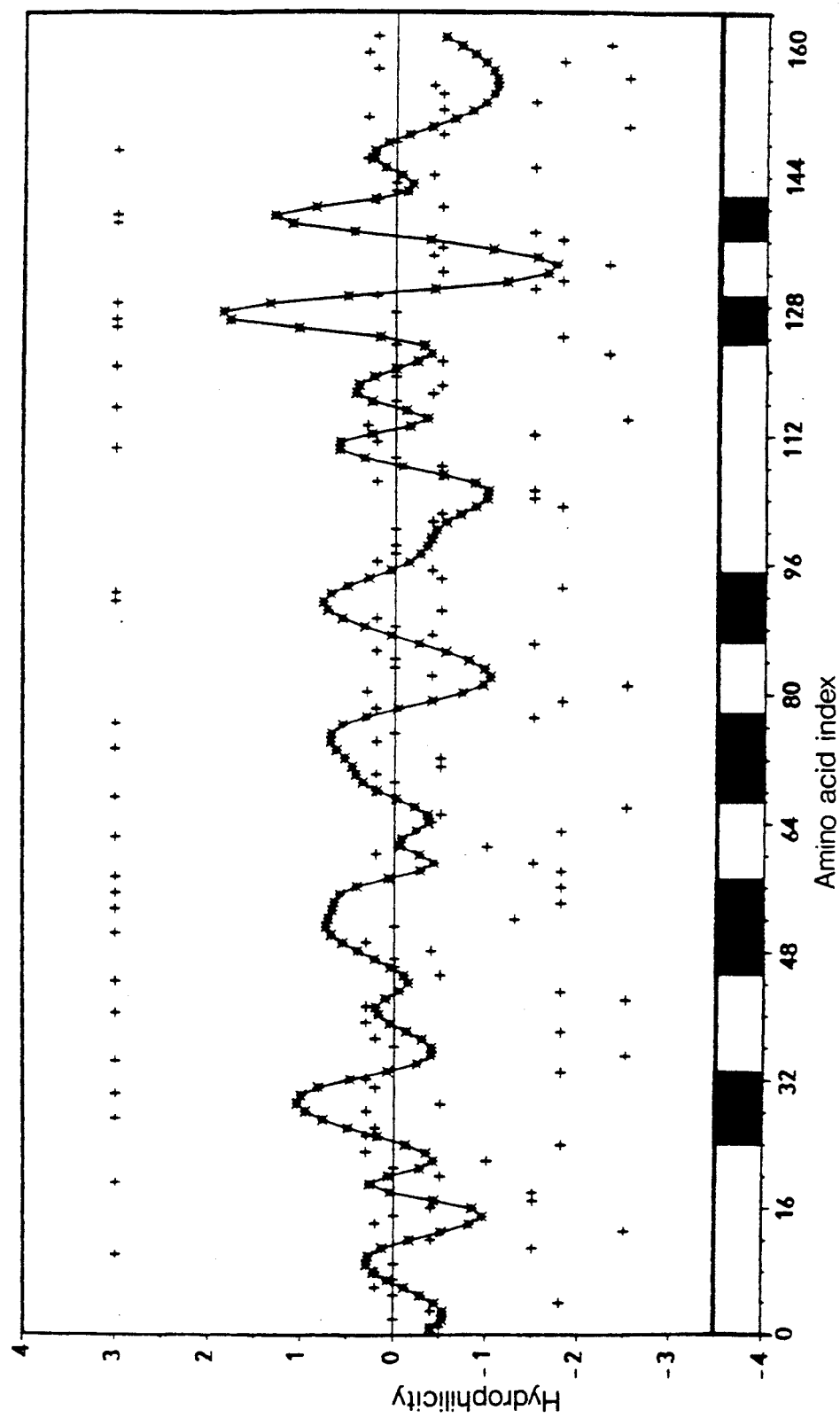
FIG. 2 presents the hydrophilicity profile of the F11 subunit based on its amino acid sequence.

In particular, it has been possible to show by investigations that *E. coli* strains which had been isolated from the affected hearts of chickens with colibacillosis produced fimbriae which were identical to fimbriae of the F11 type which also occur in *E. coli* strains which cause urinary tract infections in humans.

It has been possible to demonstrate serologically that the vast majority of the birds having an *E. coli* septicaemia had been infected with *E. coli* strains which contain fimbriae of the F11 type.

Such fimbriae contain subunit proteins having an apparent molecular weight of 18.0 kD according to SDS-PAGE.

They may be produced by wild-type avian *E. coli* strains which have been cultured on solid agar media at 37° C. but are not found if the *E. coli* is cultured in broth. Optimum expression of 18 kD fimbriae takes place if the bacteria are cultured on blood agar (base) plates (for example, of the Oxoid$^{(R)}$ make). Media which are also suitable are penassay agar plates (Difco$^{(R)}$). No 18 kD fimbriae are formed during growth at 20° C.

In the past F11 fimbriae have already been cloned from a wild-type uropathogenic *E. coli* strain (de Ree, J.M. et al., FEMS Microbiology Lett. 29, 91–97, 1985). The fimbriae-free *E. coli* K12 strain AM1727 is transformed by the plasmid pPIL 291-15 which contains the genes which code for F11 fimbriae, and said transformed strain is capable of producing F11 fimbriae. Said F11 fimbriae have now been compared with the 18 kD fimbriae which have been purified from the *E. coli* strain CH4 belonging to the 02:K1:H-serotype which frequently occurs in birds in terms of the following parameters:

a. morphology. The F11 and 18 kD fimbriae appear to be identical in the electron microscope: in both cases, the fimbriae are approximately 1 µm long and they have a diameter of approximately 7 nm;

b. molecular weight. An apparent molecular weight of 18 kD was found for the subunits of both F11 and 18 kD fimbriae by means of SDS-PAGE;

c. immunochemical specificity. In an ELISA, the F11 and 18 kD fimbriae react identically with the anti-F11 monoclonal antibodies described by de Ree, J.M. et al., J. Clin. Microbiol. 24, 121–125; 1986 and not with monoclonal antibodies against fimbriae of the F1A, F1C, F7, F7$_2$, F8, F9, F12 or F13 type;

d. amino acid composition. The amino acid composition of the 18 kD subunit is essentially identical to the composition of the F11 subunit (van Die, I. et al.; in: D.L. Lark (ed.), Proteincarbohydrate interactions in biological systems, Academic press, London, pages 39–46, 1986) (see Table 1);

TABLE 1

Comparison of amino acid composition of subunits of F11 and 18 kD *fimbriae*

| Amino acid | F11[1] | 18 kD[2] |
|---|---|---|
| Asx | 18 | 18.6 |
| Thr | 14 | 15.3 |
| Ser | 12 | 11.0 |
| Glx | 12 | 16.5 |
| Gly | 20 | 19.6 |
| Ala | 19 | 20.2 |
| Val | 13 | 12.2 |
| Ile | 6 | 5.8 |
| Leu | 10 | 10.3 |
| Tyr | 3 | 2.2 |
| Phe | 8 | 7.7 |
| Lys | 11 | 10.1 |
| Arg | 0 | 0.9 |
| His | 1 | 1.4 |
| Met | 1 | |
| Cys | 2 | |
| Pro | 6 | 6.6 |

TABLE 1-continued

Comparison of amino acid composition of subunits of
F11 and 18 kD fimbriae

| Amino acid | F11[1] | 18 kD[2] |
|---|---|---|
| Total | 161 | 161 |

[1]Calculated on the basis of the sequence (see FIG. 1)
[2]Determined by the SODIUM system using an ultrapac 8 column (LKB) after hydrolysis in 6N HCl.

e. amino-terminal amino acid sequence. The sequence of the first 17 amino acids of the amino end of the 18 kD subunit is identical to the corresponding sequence which is known for the F11 subunit (van Die, I. et al.; 1986)—FIG. 1 shows the amino acid sequence of the total F11 subunit protein. An actual molecular weight of 16.4 kD can be calculated from the sequence.

The adhesive properties of P fimbriae, like F11, can be made visible by mannose resistant hemagglutination of human erythrocytes (MRHA). This MRHA can be shown upon mixing of E. coli bacteria which express P fimbriae in sufficient amounts with human erythrocytes in the presence of mannose.

The minimum receptor structure adequate for adherence of the P fimbriae to the human erythrocytes was identified as the disaccharide Gal$\alpha$1→4Gal$\beta$ (Källenius, G. et al. Lancet ii. 604–6; 1981). Coupling of this disaccharide with latex particles results in a tool to specifically demonstrate P fimbriae on bacteria by latex agglutination (de Man, P. et al., J. Clin. Microbiol. 25, 401–6; 1987).

Recently it was shown that not F11 fimbriae themselves but special adhesins (also called "minor components" associated with the fimbriae are responsible for the adhesion (van Die, I. et al., Microbiol Pathogenesis 1, 51–56; 1986).

Table 2 shows the correlation between the expression of F11 fimbriae and the adhesion characteristics of a uropathogenic E. coli strain, an F11 fimbriae producing recombinant clone and a number of E. coli strains isolated from afflicted hearts of chicken suffering from colibacillosis are compared. From this table it can be concluded that the F11 fimbriae of E. coli isolated from the chicken recognize at least the same receptor as the F11 fimbriae of human E. coli.

TABLE 2

Expression of F11 fimbriae, hemaggloutination and P-receptor recognition.

| Strain number[a] (Serotype) | Expression of F11 fimbriae measured in | | Adhesion measured in | |
|---|---|---|---|---|
| | ELISA[b] | Western[c] blotting | MRHA test[d] | P-receptor test[e] |
| H291 (0.1:K1) | >4.7 | ++ | +++ | ++ |
| AM1727 | — | — | — | — |
| AM1727/ pPIL291-15 | >4.7 | +++ | ++++ | ++++ |
| CH2 (078:K80) | 3.0 | + | + | + |
| CH4 (02:K1) | >4.7 | ++ | ++ | ++ |
| CH5 (02:K1) | 2.7 | — | — | — |
| CH6 (01:K1) | >4.7 | ++ | ++ | ++ |
| CH7 (015:K14) | — | — | — | — |
| CH96 (078:K80) | 3.2 | + | ++ | + |
| CH139 (02:K1) | <4.7 | ++ | +++ | +++ |

[a]H291 is human E. coli, F11 reference strain C1976; AM1727/pPIL291-15 is a F11-fimbriae producing recombinant clone of the fimbriae-less K12 strain AM1727; CH numbers are E. coli strains isolated from chicken suffering from colibacillosis.
[b]whole bacteria ELISA with anti-F11 serrnum; [10]log titers defined as the highest serum dilution having an A$_{540}$ value of at least two times the background value.
[c]Western blotting of crude fimbriae preparation with anti-F11 serum.
[d]Mannose resistant hemagglutination with human erythrocytes;
[e]Agglutination of latex particles coated with Gal$\alpha$1 → 4Gal$\beta$.
Meaning of symbols:
—:no reactivity in above mentioned tests
+through ++++: increasing degrees of reactivity in above-mentioned tests.

The vaccine according to the invention may also contain, together with or instead of F11 fimbriae, immunogenic sections of F11 fimbriae. Such immunogenic sections may, for example, be understood to mean the 18 kD subunits, aggregates thereof, or fragments thereof or adhesins characteristic for F11 fimbriae, or aggregates, or fragment thereof. Such a fragment of an 18 kD subunit or a F11 adhesin of the type referred to may be a polypeptide which contains one or more epitopes which are capable of stimulating protective antibodies against E. coli of the F11 type in poultry.

Suitable polypeptide fragments of 18 kD subunits or F11 adhesins can be found, for example, by means of techniques known per se. Such a technique has been described by T.P. Hopp and K.R. Woods (Prediction of protein antigenic determinants from amino acid sequences; Proc. Natl. Acad. Sci. 78, 3824–3828; 1981) by determining the mean hydrophilicity of consecutive segments of the amino acid chain. The results of such a determination are shown in FIG. 2. In this figure the hydrophilicity profile of the F11 subunit based on the known amino acid sequence is represented. The profile plotted therein shows the progessive weighted mean value of the hydrophilicity over every 7 amino acids. The regions with the most pronounced hydrophilicity are considered as the regions which probably constitute antigenic determinants. In FIG. 2 these regions are indicated by black blocks, and they correspond to the amino acid segments:

| 24-33 | Ile—Ser—Gln—Lys—Ser—Ala—Asp—Gln—Ser—Ile |
| 45-47 | Ala—Gly—Gly—Thr—Ser—Lys—Pro—Met—Asp—Leu—Asp—Ile—Glu |
| 67-78 | Lys—Gln—Gly—Gln—Ala—Ala—Lys—Asn—Gly—Lys—Val—Gln |
| 87-95 | Thr—Gly—Gln—Ala—Glu—Glu—Leu—Ala—Thr |
| 123-130 | Pro—Leu—Lys—Asp—Gly—Asp—Asn—Val |
| 136-142 | Leu—Val—Lys—Lys—Ala—Asn—Gly. |

It is to be expected that the antigenic determinants of the 18 kD subunits of F11 fimbriae are also located in these regions. Similar conclusions were reached by I. van Die, W. Hoekstra and H. Bergmans (Microbiol. Pathogenesis 3, 149–154; 1987) for the F11 fimbriae using the same model.

Suitable immunochemically active polypeptide fragments of 18 kD subunits or F11 adhesines can also be found by means of the method described in Patent Application WO 84/03506—the so-called pep-scan method, wherein a series of partially overlapping polypeptides corresponding with partial sequences of the protein under consideration, are synthesized and their reactivity with antibodies is investigated.

In order to increase the immunogenic nature, such a polypeptide fragment may optionally be bound to a carrier.

The F11 fimbriae or immunogenic sections thereof can be prepared by separating the fimbriae in a known manner from a wild-type *E. coli* strain of the F11 type or a derivative thereof and optionally isolating an immunogenic section thereof.

F11 fimbriae or immunogenic sections thereof may also be produced by starting from cells which have been transformed with recombinant DNA which contains the genetic material which codes for the production and, optionally, excretion of F11 fimbriae or immunogenic sections thereof.

In addition, it is also possible, in particular in the case of smaller polypeptide fragments, to prepare them completely synthetically by means of, for example, the Merrifield method which makes use of a solid phase.

The vaccine according to the invention can also contain an organism in which there is genetic material which codes for the production and/or secretion of F fimbriae or an immunogenic section thereof.

Preferably, this will involve apathogenic organisms.

These organisms are able by their nature to produce said antigenic material, or have recombinant polynucleotide which codes for the desired antigenic material.

Viruses or bacteria may be used, inter alia, as such recombinant organisms. Said recombinant organisms may themselves be able to produce the desired antigenic material and optionally to excrete it.

The vaccine according to the invention is preferably administered parenterally, for example subcutaneously or intramuscularly. The vaccine may be administered in this manner both for the active immunization of the vaccinated birds and to laying birds for the passive immunization of the offspring thereof. In immunized laying birds, the antibodies raised in them will, of course, be introduced into the yolks of their eggs and therefore subsequently in the hatched chicks.

The vaccine according to the invention may also be administered orally, intranasally or by inhaling an aerosol—in this case the vaccine may preferably contain live apathogenic organisms in which there is genetic material which codes for the production and excretion of F11 fimbriae or immunogenic sections thereof.

A vaccine according to the invention may be prepared by first providing for proteins or polypeptides derived therefrom, or the production of F11 fimbriae or microorganisms containing these F11 fimbriae, proteins or polypeptides, as described above.

The latter case wherein the fimbriae are obtained from *E. coli* is the most preferred embodiment. In general, after culturing the *E. coli* having F11 fimbriae, the latter are separated from the bacteria, e.g. by mechanical detachment (shearing) and/or heating, and removal of the cells (by centrifugation and/or (ultra) filtration). Subsequently the fimbriae can be further purified by removal of contaminations from the culturing medium and/or the bacterial membrane, e.g. by ultrafiltration, column chromatography or specific precipitation (using ammonium sulphate, or other salts, or by changing the pH to the isolectric point of the fimbriae).

For parenteral vaccination, the active component is in general contained in an aqueous solution or suspension, often mixed with other constituents in order to increase the activity or the shelf life, such as salts, formalin, pH buffers, emulsifiers and adjuvants to improve the immune response. Suitable adjuvants are, for example, mineral oils, muramyl dipeptide, aluminium hydroxide, saponin, polyanions and amphipatic substances.

Both the composition of the vaccine and the vaccination system can be varied and depend on the type of bird to be protected, the age and the weight of the bird, the desired duration of protection, the method of administration and on the question of whether active immunization or passive immunization by means of maternal antibodies is desired. The effective quantity of the active component in the vaccine is approximately 10–100 $\mu$g per dose for parenteral vaccination.

The above described active immunisation against *E. coli* having F11 fimbriae primarily will be applied as a protective treatment in healthy birds. It goes without saying that birds already infected by *E. coli* having F11 fimbriae suitably can be treated with antibodies directed against F11 fimbriae, or sections or aggregates thereof.

EXAMPLE 1

Purification of Fimbriae

To purify fimbriae, three wild-type *E. coli* strains were cultured for one night on a blood agar base (Oxoid$^{(R)}$) plates at 37° C. For this purpose, the CH2(078:K80:H4), CH4(02:K2:H-) and CH6(01:K1:H-) *E. coli* strains were used which were isolated from the affected hearts of chickens suffering from colibacillosis. The F11 fimbriae clone AM1727 - pplL291-15 (De Ree et al., 1985) was also cultured for 16 hours in a Biostat$^{(R)}$ fermentor (Braun) in a "Brain Heart Infusion" broth containing 50 $\mu$g/ml ampicillin at a constant temperature of 37° C., a pH of 7.4 and an oxygen saturation of approximately 40%.

The bacteria were harvested in 10 mM Tris-HCl buffer with a pH of 7.5.

The fimbriae were released from the bacteria by either treating the bacteria consecutively for 15 times for 1 minute on ice in a Sorval Omnimixer; or heating the bacteria for 15 minutes at 65° C.; or subjecting the bacteria to a combination of the two treatments mentioned above.

The bacteria were then removed by centrifuging and filtering, the crude fimbriae solution was concentrated, and the fimbriae were intensively washed in an Amicon cell provided with a YM 100 filter.

The fimbriae were subsequently purified, for example, by means of a somewhat modified method as described by Korhonen et al. (Infect. Immun. 27, 568–575, 1980) which amounts to precipitating the fimbriae with ammonium sulphate, dissolving them with sodium deoxycholate and centrifuging them in a sucrose gradient.

The fimbriae preparations purified in this manner exhibited identical fimbriae structures on electronmicroscopy (as described by Van den Bosch, J.F. et al., Infect. Immun. 29, 226–233, 1980). All fimbriae preparations showed one single band at 18kD in SDS-PAGE (as described by Lugtenberg, B. et al., FEBS Lett. 58, 254–258, 1975) and in Western blotting (as described by Muilerman, H.G. et al., Anal. Biochem. 120, 46–51, 1982) with all antisera raised against the various fimbriae.

EXAMPLE 2

A. A vaccine containing fimbriae according to the invention was prepared as a water-in-oil emulsion based on a mineral oil (low-viscosity paraffin) with polysorbate 80 and sorbitan monooleate as emulsifiers.

B. A vaccine was prepared as in 2A which contained 50 μg/ml F11 fimbriae purified from the wild-type CH4(02:K1:H-) E. coli strain.

C. A vaccine was prepared as in 2A which contained 50 μg/ml F11 fimbriae purified from the clone AM1727-ppIL291-15. Samples of this clone were deposited in the Collection Nationale de Cultures de Microorganismes of the Pasteur Institute in Paris under no. I-709 on Oct. 19, 1987.

EXAMPLE 3

Active Immunization

For active immunization experiments, a vaccine was prepared as in Example 2, intramuscularly injected into the birds under investigation, and the development of specific anti-fimbriae serum antibody titres was determined by means of an ELISA.

A. ELISA

For the ELISA, PVC microtitre plates were incubated for one night at room temperature with 100 μl of a purified fimbriae solution prepared as in Example 1 containing 2.5 μg fimbriae per ml of 0.04M PBS (pH 7.2) in each well.

The plates were then treated by incubating them for 20 minutes at 37° C. with 200 μl of a 5% BSA solution in PBS in each well, washing them with water and drying in air. The anti-fimbriae sera were investigated by incubating 100 μl of serial dilutions of the serum in a buffer (pH 7.4, 0.2M Na$_2$HPO$_4$, 0.2M NaCl, 0.1% BSA and 0.05% Tween 80) in each well for 1 hour at 37° C.

After washing, the plates were incubated for 30 minutes with 100 μl of diluted conjugate (rabbit anti-chicken IgG/Po (H+L), Nordic), in each well and then washed once again.

The antibody activity was determined colorimetrically by adding to each well 100 μl of an enzymesubstrate solution (containing 15 ml of distilled water, 1.5 ml of a 0.14% urea peroxide solution in sodium acetate/citric acid buffer (pH 5.5) and 0.2 ml of a 0.6% TMB solution in DMSO).

The enzymatic reaction was carried out in the dark and stopped after 10 minutes by adding 50 μl of 4N H$_2$SO$_4$ per well, and the absorption was subsequently measured at 450 nm (A$_{450}$) in a Microelisa[R] Reader (Organon Teknika).

The first serum dilution was 1:50. The background was measured in each plate by incorporating serum obtained before vaccination and diluted in the ratio of 1:50 in at least 8 wells. The antibody titre was defined as the maximum serum dilution which yielded an A$_{450}$ of at least 1.15 times the mean A$_{450}$ background.

Vaccination of SPF Broilers 6-week old SPF boilers (Gezondheidsdienst voor Pluimvee (Poultry Health Service), Doorn, Netherlands) were intramuscularly injected with 1 ml of vaccine as prepared in Example 2B. 4 weeks later, a booster injection was given using the same material. The results are shown in Table 3.

TABLE 3

Serum antibody production after vaccinating 6-week old broilers; logarithms of ELISA titers

| Chicken number | weeks after first injection | | | | |
|---|---|---|---|---|---|
| | 0 | 2 | 4* | 6 | 8 |
| 1 | <1.7 | 3.2 | 4.4 | 4.1 | 4.7 |
| 2 | <1.7 | 3.8 | 4.4 | 4.1 | 4.7 |
| 3 | <1.7 | 3.2 | >4.7 | 4.7 | 4.7 |
| 4 | <1.7 | 4.4 | >4.7 | >4.7 | >4.7 |
| 5 | <1.7 | 4.4 | >4.7 | >4.7 | >4.7 |

*booster injection

C. Vaccination of Broiler Breeding Hens

Two groups each containing 8 broiler breeding hens 20 weeks old (Euribrid, Boxmeer, Netherlands) were intramuscularly injected with 1 ml of the vaccine as prepared in Examples 2B and 2C respectively. Six weeks after the first injection, a booster injection was given using the same respective vaccines. As is evident from Table 4, a high antibody production was found in the serum of the broiler breeding hens, accompanied by the transfer of antibodies to egg yolks and serum of hatched chicks.

TABLE 4

Antibody production after vaccination of 20-week old broiler breeding hens: mean logarithm of ELISA titres (±SD) in serum of breeding hens, egg yolk and serum of hatched chicks.

| Fimbriae purified from strain | Serum of broiler breeding hens[1] | Egg yolk[2] | Serum of hatched chicks[3] |
|---|---|---|---|
| CH4(02:K1:H-) | 4.58 ± 0.50 | 5.29 ± 0.39 | 3.98 ± 0.27 |
| AM1727-pPIL291-15 | 5.48 ± 0.21 | 5.14 ± 0.47 | 4.16 ± 0.39 |

[1] serum samples taken 10 weeks after first injection
[2] mean of 8 eggs taken 11 weeks after first injection
[3] mean of 5 one-week old chickens hatched from eggs taken 12 weeks after the first injection.

Identical results were obtained for vaccination with F11 fimbriae of the CH4 strain and of the clone AM1727-ppIL291-15. Complete cross-reaction between the two preparations was found in an ELISA.

EXAMPLE 4

Protection of Broilers by Vaccination of Breeding Hens

Broiler breeding hens were vaccinated with F11 fimbriae purified from the clone AM1727-pPIL291-15 (see example 3C).

Broiler chicks hatched from these vaccinated breeding hens and from non-vaccinated control hens were challenged at an age of 3 weeks by injection of 0.2 ml of bacterial suspensions into the right posterior thoracic air sac. The bacterial strains used were all isolated from affected hearts of chickens with colibacillosis. Bacteria were cultured overnight on blood agar base plates (Oxoid[R]), suspended in PBS to the appropriate concentration. The broiler chicks were housed in reduced-pressure isolators with food and water ad lib.

As shown in Table 5, good protection was transferred from vaccinated breeding hens to the hatched broiler chicks. Compared to the non-vaccinated controls, for all strains taken together the efficacy of protection by vaccination with F11 fimbriae was 85%.

It is striking that protection was conferred also against challenge with strain CH7 which seemingly does not express F11 fimbriae in vitro. It might be possible that this strain does in fact express F11 fimbriae in vivo, but that in vitro expression is below the limit of detection for the methods used.

infection (Table 6). The protection against infection with CH6 strain was fairly low, although this strain

TABLE 5

Protection against *E. coli* challenge of broilers hatched from breeding hens that were vaccinated with F11 *fimbriae*

| | Challenge with strain[1]: | | | | | | |
|---|---|---|---|---|---|---|---|
| Vaccine | CH2 078:K80 F11+ ($5 \times 10^6$) | CH4 02:K1 F11+ ($2 \times 10^6$) | CH5 02:K1 F11+ ($10^6$) | CH6 01:K1 F11+ ($5 \times 10^6$) | CH7 015:K14 F11− ($10^6$) | CH245 035:K- F11+ ($5 \times 10^6$) | All strains |
| F11 | 2/10[2] | 2/10 | 1/10 | 0/10 | 0/10 | 1/10 | 6/60[3] |
| Control | 6/10 | 6/10 | 10/10 | 5/10 | 7/10 | 5/10 | 39/60[3] |

[1] For each strain serotype, F11 expression and challenge dosis are indicated
[2] Number of dead chickens within 7 days after challenge/total challenged.
[3] Chi-square test: $P < 0.0001$

EXAMPLE 5

Protection of Broilers by Passive Immunization

Antisera were prepared by inoculating rabbits with purified F11 fimbriae and then inactivating for 30 minutes at 56° C.

1 ml of this undiluted F11 antiserum was injected intravenously into three-week old broilers (Euribrid, Boxmeer, Netherlands).

Within 1 hour after intravenous injection with antiserum, the chicks were injected by injection of 0.2 ml of bacterial suspension into the right posterior thoracic air sac. As a control, chicks to which no antiserum had been administered were infected with the same dose of bacteria. The bacterial strains used were all isolated from affected hearts of chickens with colibacillosis. The bacteria were cultured for one night on blood agar base plates (Oxoid(R)), suspended in PBS and diluted to the appropriate concentration.

The chickens were housed in reduced-pressure isolators with food and water ad lib.

From these experiments it was evident that F11 fimbriae antiserum offers good protection to broilers against 5 of the 6 *E. coli* strains which were used for the produces F11 fimbriae. Possibly this strain produces, in addition to F11 fimbriae, also one or more other powerful virulence factors but it is also possible that the antibody level was simply too low to provide protection against this strain of bacteria.

A striking feature is that considerably protection was achieved against infection even with the CH7 strain which does not appear to produce any F11 fimbriae itself. Possibly this strain does in fact produce F11 fimbriae in vivo but the F11 fimbriae production in vitro is too low for the method of detection used.

TABLE 6

Protection of broilers against *E. coli* infection by passive immunization with F11 *fimbriae* antiserum

| Infection with strain | | Dose | Anti-F11 antiserum administered | No. of chickens dead within 7 days after infection/total | $P < 0.05$* |
|---|---|---|---|---|---|
| No. | Serotype | | | | |
| CH2 | 078:K80:H4:F11+ | $5 \times 10^6$ | + | 2/17 | + |
| CH2 | | $5 \times 10^6$ | − | 15/17 | |
| CH5 | 02:K1:H7:F11+ | $10^6$ | + | 0/8 | + |
| CH5 | | $10^6$ | − | 6/9 | |
| CH6 | 01:K1:H-:F11+ | $10^7$ | + | 13/24 | |
| CH6 | | $10^7$ | − | 19/29 | |
| CH7 | 015:K14:H10:F11− | $2 \times 10^6$ | + | 1/8 | + |
| CH7 | | $2 \times 10^6$ | − | 6/9 | |
| CH245 | 035:K-:H?:F11+ | $5 \times 10^6$ | + | 2/17 | + |
| CH245 | | $5 \times 10^6$ | − | 11/19 | |

Chi-square test

I claim:

1. Method for protecting poultry against *E. coli* air sac inflammation and septicaemia, comprising administering an effective amount of a vaccine comprising an *E. coli* immunogen consisting essentially of at least one purified immunogenic component selected from the group consisting of fimbriae of the F11 type, an immunogenic section thereof, and an organism in which there is expressible genetic material which codes for the production of said fimbriae or an immunogenic section thereof and a pharmaceutically acceptable carrier or diluent.

* * * * *